(12) United States Patent
Sun et al.

(10) Patent No.: US 9,140,641 B2
(45) Date of Patent: Sep. 22, 2015

(54) FLUID ANALYSIS METHOD AND FLUID ANALYSIS SYSTEM

(71) Applicant: National Taiwan University, Taipei (TW)

(72) Inventors: Chen-Li Sun, Taipei (TW); Tzu-Hsun Hsiao, Keelung (TW); Chien-Yuan Huang, New Taipei (TW)

(73) Assignee: National Taiwan University, Taipei (TW)

( * ) Notice: Subject to any disclaimer, the term of this patent is extended or adjusted under 35 U.S.C. 154(b) by 145 days.

(21) Appl. No.: 14/135,585

(22) Filed: Dec. 20, 2013

(65) Prior Publication Data

US 2015/0048264 A1 Feb. 19, 2015

(30) Foreign Application Priority Data

Aug. 13, 2013 (TW) .............................. 102128919 A (51) Int. Cl.
*G01N 21/41* (2006.01)
*G01N 21/17* (2006.01)
*G01N 21/45* (2006.01)

(52) U.S. Cl.
CPC ................ *G01N 21/17* (2013.01); *G01N 21/45* (2013.01); *G01N 2021/1765* (2013.01)

(58) Field of Classification Search
CPC ....................... G01N 2021/1765; G01N 21/17; G01N 21/45
See application file for complete search history.

(56) References Cited

U.S. PATENT DOCUMENTS

| | | | |
|---|---|---|---|
| 4,993,832 A | 2/1991 | Pawliszyn | |
| 5,153,666 A | 10/1992 | Pawliszyn | |
| 6,181,416 B1 | 1/2001 | Falk | |
| 6,891,980 B2 | 5/2005 | Gerhard et al. | |
| 8,462,326 B2 * | 6/2013 | Liu et al. ....................... | 356/129 |

FOREIGN PATENT DOCUMENTS

| | | |
|---|---|---|
| TW | 201219772 | 5/2012 |
| TW | M436897 | 9/2012 |
| TW | I409452 | 9/2013 |

OTHER PUBLICATIONS

Chen-li Sun and Tzu-hsun Hsiao, "Quantitative analysis of microfluidic mixing using microscale schlieren technique," Microfluidics and Nanofluidics, vol. 15, Issue 2, Feb. 15, 2013, pp. 1-14.

* cited by examiner

*Primary Examiner* — Tony Ko
(74) *Attorney, Agent, or Firm* — Jianq Chyun IP Office (57) ABSTRACT

A fluid analysis method is provided. A gradient distribution of a first scalar property of a calibration fluid in a space is obtained. A calibration schlieren image of the calibration fluid is acquired and processed to obtain an intensity distribution of the calibration schlieren image. The gradient distribution of the first scalar property of the calibration fluid in the space is mapped to the intensity distribution of the calibration schlieren image, so as to obtain a corresponding relation between the gradients of the first scalar property and the intensities. A test schlieren image of a test fluid is acquired and processed to obtain intensity distribution of the test schlieren image. The intensity distribution of the test schlieren image is converted to the gradient distribution of the first scalar property of the test fluid according to the corresponding relation. Moreover, a fluid analysis system is also provided.

24 Claims, 7 Drawing Sheets

FLUID ANALYSIS METHOD AND FLUID ANALYSIS SYSTEM

CROSS-REFERENCE TO RELATED APPLICATION

This application claims the priority benefit of Taiwan application serial no. 102128919, filed on Aug. 13, 2013. The entirety of the above-mentioned patent application is hereby incorporated by reference herein and made a part of this specification.

BACKGROUND

1. Technical Field

The invention relates to an analysis method and an analysis system. Particularly, the invention relates to a fluid analysis method and a fluid analysis system.

2. Related Art

When developing a micro total analysis system (µTAS), it is vital and indispensible to be able to analyze the properties inside the microfluidics in order to incorporate the micro total analysis system to a boarder and more complex line of designs.

However, the analysis methods commonly used in pervious studies are limited to either two-dimensional or steady measurements. For example, although a micro-particle imaging velocimetry (µPIV) technique or a fluorescent method may provide velocity measurements or mixing quantitation of a full flow field, it is only applicable to two-dimensional (2D) measurements. On the other hand, a confocal laser scanning microscopy technique can be applied to the three-dimensional (3D) measurements. Nevertheless, it is flawed by the vast cost and the limitation of the slow scanning rate.

SUMMARY

The invention is directed to a fluid analysis method, by which at least one scalar property of a fluid is analyzed.

The invention is directed to a fluid analysis system, which analyzes at least one scalar property of a fluid.

An embodiment of the invention provides a fluid analysis method, which includes the following steps. The gradient distribution of the first scalar property of the calibration fluid in a calibration channel is obtained. A calibration schlieren image of the calibration fluid is captured and processed to obtain the light intensity distribution of the calibration schlieren image. The gradient distribution of the first scalar property of the calibration fluid is then mapped to the light intensity distribution of the schlieren image in order to obtain the correlation between the gradients of the first scalar property and the light intensities of the schlieren image. The light intensity distribution of a test fluid in a test channel is then transformed to the gradient information of the first scalar property of this specific test fluid by the correlation between the gradients of the first scalar property of the calibration fluid and the light intensities of the schlieren image with the calibration fluid.

An embodiment of the invention provides a fluid analysis system comprising a schlieren image-detecting device and a processing unit. The schlieren image-detecting device consists of a light source, an objective lens, a knife-edge and an image-capturing module. The light source provides a light beam. The objective lens is placed on the transmission path of the light beam. The knife-edge is located on the transmission path of the light beam, and is located at the back focal plane of the objective lens. The image-capturing module is configured to acquire and record a calibration schlieren image of a calibration fluid and a test schlieren image of a test fluid. The processing unit is electrically connected to the image-capturing module, and is configured to receive and process the calibration schlieren image and the test schlieren image. The processing unit handles the calibration schlieren image of the calibration fluid in a calibration channel to obtain an intensity distribution of the calibration schlieren image. The processing unit also obtains the gradient distribution of the first scalar property of the calibration fluid in the calibration channel, and corresponds the gradient distribution of the first scalar property of the calibration fluid to the distribution of light intensity of the calibration schlieren image, so as to obtain a relation between the gradients information of the first scalar property and the light intensities. The processing unit handles the test schlieren image of the test fluid to obtain distribution of light intensity of the test schlieren image, and converts the distribution of light intensity of the test schlieren image to the gradient distribution of the first scalar property of the test fluid according to the correlation between the gradients information of the first scalar property and the light intensities.

In an embodiment of the invention, the procedures of obtaining the gradient distribution of the first scalar property of the calibration fluid in calibration channel comprise: obtaining a spatial distribution of the first scalar property of the calibration fluid in calibration channel; and calculating the corresponding gradient distribution of the first scalar property of the calibration fluid in calibration channel from processing the spatial distribution of the first scalar property.

In an embodiment of the invention, the steps of obtaining the gradient distribution of the first scalar property of the calibration fluid include the following procedures: the processing unit obtains a spatial distribution of the second scalar property of the calibration fluid in calibration channel, calculates the gradient distribution of the second scalar property of the calibration fluid, and obtains the gradient distribution of the first scalar property of the calibration fluid according to the relation between the second scalar property and the first scalar property of the calibration fluid.

In an embodiment of the invention, the fluid analysis method further includes calculating the gradient distribution of the second scalar property of the test fluid according to the relation of the second scalar property and the first scalar property of the test fluid.

In an embodiment of the invention, a method for obtaining the calibration schlieren image or the test schlieren image includes the following procedures: A Hoffman modulation contrast microscope is provided. The Hoffman modulation contrast microscope has a modulator located at the back focal plane of the objective lens of the Hoffman modulation contrast microscope. The modulator is replaced with a knife-edge to construct a schlieren image-detecting device. The schlieren image-detecting device is used to acquire the calibration schlieren image or the test schlieren image.

In an embodiment of the invention, wherein the pixel pitch on the calibration schlieren image of the calibration fluid corresponds to a distance varying between 60 nm and 19.1 µm, and the pixel pitch on the test schlieren image of the test fluid corresponds to a distance varying between 60 nm to 19.1 µm.

In an embodiment of the invention, the calibration fluid and the test fluid are solutions, and the first scalar property is concentration.

In an embodiment of the invention, the refractive indices of both the test fluid and the calibration fluid vary linearly with the first scalar property of the test fluid and the calibration fluid respectively, in at least part of the range of the first scalar property of the test fluid and the calibration fluid.

In an embodiment of the invention, solvents of the calibration fluid and the test fluid are identical, and solutes of the calibration fluid and the test fluid are also identical.

In an embodiment of the invention, compositions of the calibration fluid and the test fluid are different; the first scalar property is refractive index, and the second scalar property can be concentration or temperature.

In an embodiment of the invention, the first scalar property includes temperature.

In an embodiment of the invention, the calibration channel is a T-shaped microchannel into which the calibration fluid is drawn with a known flow rate.

In an embodiment of the invention, the processing unit obtains a spatial distribution of the first scalar property of the calibration fluid, and calculates the gradient distribution of the first scalar property from the spatial distribution of the first scalar property of the calibration fluid.

In an embodiment of the invention, the processing unit obtains a spatial distribution of the second scalar property of the calibration fluid, calculates the gradient distribution of the second scalar property from the spatial distribution of the second scalar property of the calibration fluid, and obtains the gradient distribution of the first scalar property of the calibration fluid from the relation between the second scalar property and the first scalar property of the calibration fluid.

In an embodiment of the invention, the processing unit obtains the gradient distribution of the second scalar property of the test fluid according to a relation between the second scalar property and the first scalar property of the test fluid.

In an embodiment of the invention, the space which the calibration fluid is filled up with is a T-shaped microchannel, and the fluid analysis system further comprises at least one syringe pump so as to draw the calibration fluid into the T-shaped micro channel.

The distance between two adjacent pixels of the calibration schlieren image acquired by the image-capturing module corresponds to a length varying from 60 nm to 19.1 μm, and the distance between two adjacent pixels of the test schlieren image acquired by the image-capturing module corresponds to a length varying from 60 nm to 19.1 μm.

In an embodiment of the invention, the schlieren image-detecting device further includes a micropositioner, which is configured to adjust the cutoff degree of the knife-edge.

Abiding from the aforementioned principles, the invention is a group of fluid analysis system and method which measures the gradient distribution of the first scalar property in a flow field from the relation between the light intensities of schlieren image and the gradients information of the first scalar property. Moreover, the invention of the fluid analysis system and method is able to reveal the three-dimensional structure of the flow field by analyzing the gradient information of the first scalar property. The discernible details of the acquired image are greatly enhanced which enables this invention to surpass other measurement methods. This invention provides a novel, full-field, transient, and non-invasive measurement method for heat and mass transfer in micro fluidics.

In order to make the aforementioned features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute as part of this specification. The drawings illustrate embodiments of the invention and, together with the description, serve to explain the principles of the invention.

DETAILED DESCRIPTION OF DISCLOSED EMBODIMENTS

Figure 1A:
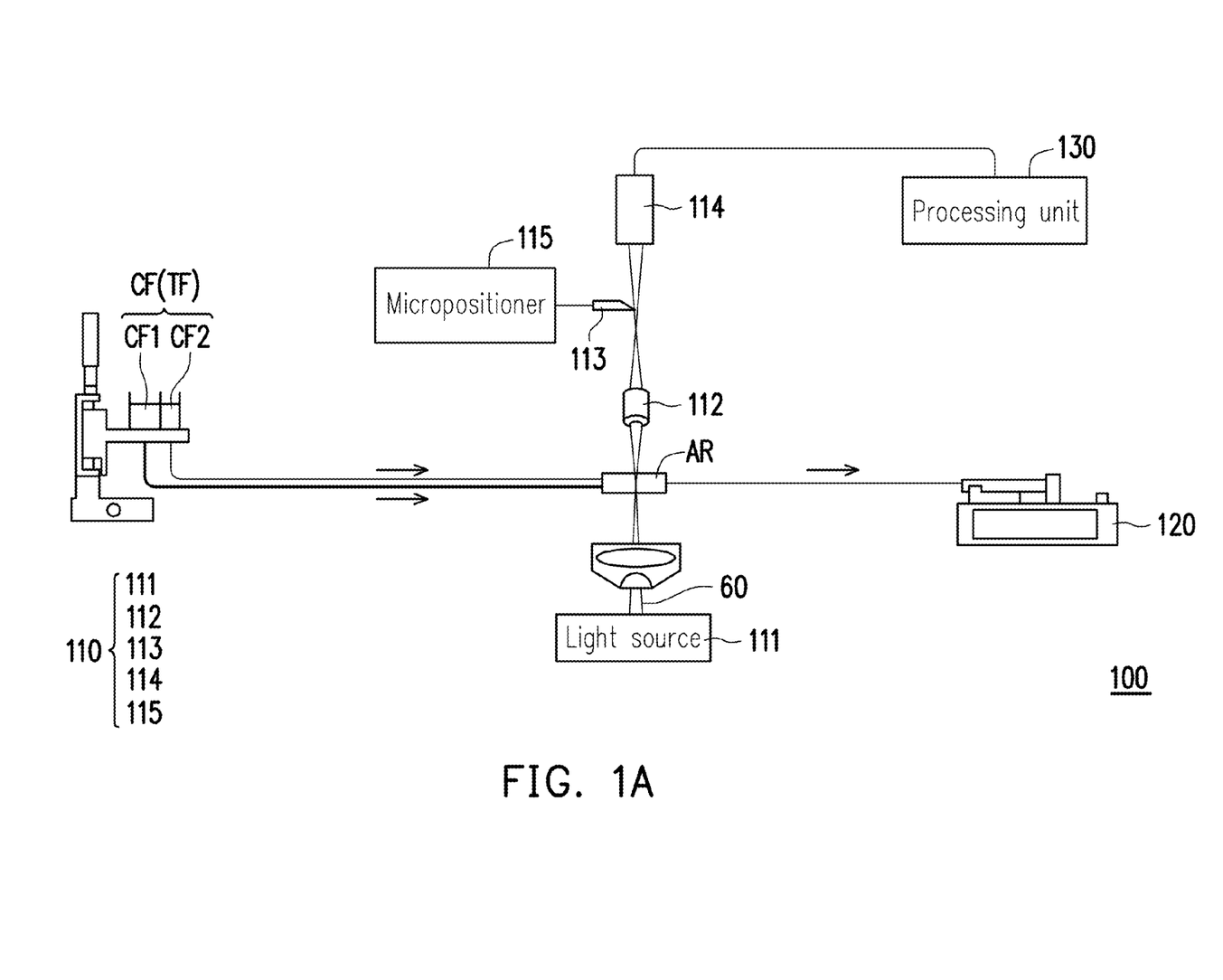
FIG. 1A is a schematic diagram of a fluid analysis system according to an embodiment of the invention.
Figure 1B:
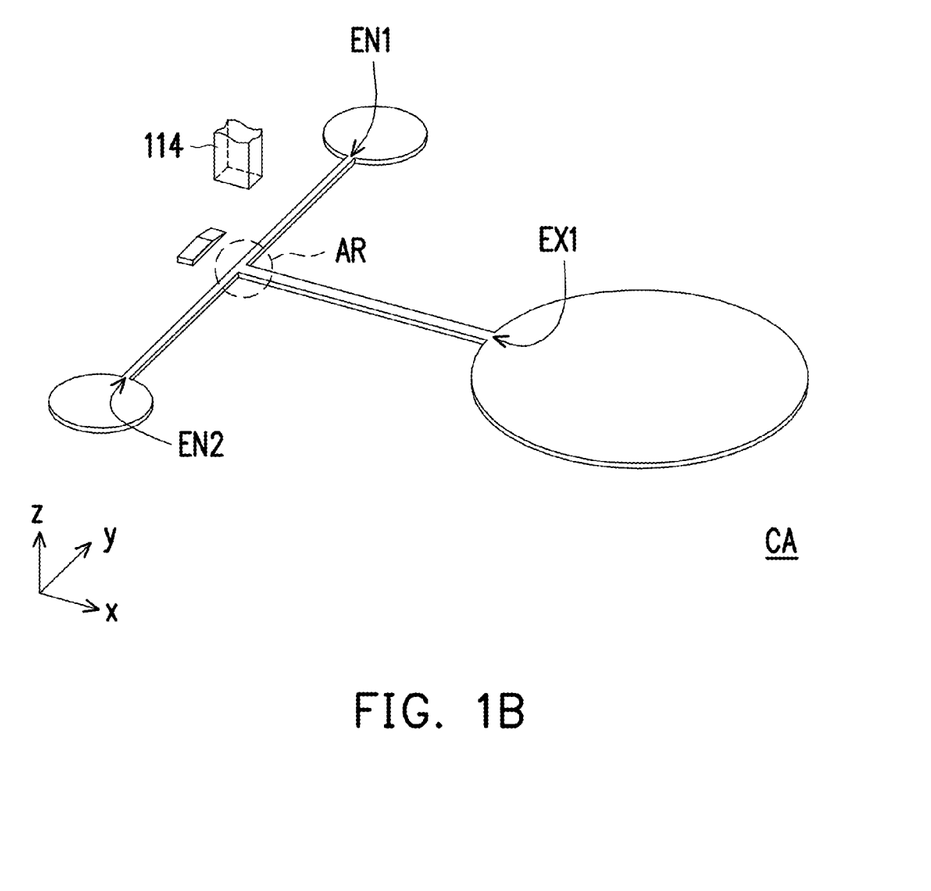
FIG. 1B is a schematic diagram of a T-shaped microchannel as part of the fluid analysis system in FIG. 1A.

FIG. 1A is a schematic diagram of the fluid analysis system according to an embodiment of the invention. FIG. 1B is a schematic diagram of a T-shaped microchannel as part of the fluid analysis system in FIG. 1A. Referring to FIG. 1A, the fluid analysis system 100 of the present embodiment includes a schlieren image-detecting device 110, at least one syringe pump 120 and a processing unit 130. Detailed descriptions are as follows. In the present embodiment, the schlieren image-detecting device 110 includes a light source 111, an objective lens 112, a knife-edge 113 and an image-capturing module 114. In the present embodiment, the light source 111 is, for instance, a light emitting diode (LED) light source, and the image-capturing module 114 may include a charge-coupled device (CCD) camera and a image capturing card.

Furthermore, the fluid analysis system 100 of the present embodiment may use the syringe pump 120 to drive a calibration fluid CF or a test fluid TF to flow into a space AR. In the present embodiment, the calibration fluid CF and the test fluid TF are solutions, and the compositions of the calibration fluid CF and the test fluid TF can either be identical or different; the invention is not limited to the composition of the test fluid. In detail, as shown in FIG. 1B, AR represents either the calibration channel or a test channel. The calibration channel is a T-shaped microchannel in the present embodiment. In other words, in the present embodiment, the syringe pump 120 can be configured to drive the calibration fluid CF or a test fluid TF to flow into the T-shaped microchannel or a test channel, respectively. Moreover, in the present embodiment, the casing CA that forms the T-shaped microchannel is fabricated from pouring polydimethylsiloxane (PDMS) over a master mold of negative photoresist with predefined pattern. The two entrances of the T-shaped microchannel are both 90 μm wide and 2500 μm long. The flow channel after convergence is 180 μm wide and 3000 μm long. The T-shaped microchannel is 55.2 μm throughout. It should be taken into notice that the aforementioned parameters are only used as examples in illustrations, not to limit the invention.

In detail, in the present embodiment, the light source 111 of the schlieren image-detecting device 110 provides a light beam 60. The objective lens 112 and the knife-edge 113 are both placed on a transmission path of the light beam 60, and the knife-edge 113 is also located at the back focal plane of the objective lens 112. Since the back focal plane of a conventional microscope can not be easily accessed, it is hard to place the knife-edge 113 at proper location in conventional microscope. However, in the present embodiment, the method of locating the knife-edge 113 at the back focal plane of the objective lens 112 can be easily implemented in a Hoffman modulation contrast microscope. In detail, the Hoffman modulation contrast microscope has a modulator (not shown) that is located at its back focal plane. Therefore, in the present embodiment, the modulator can be replaced by the knife-edge 113 to conveniently form the schlieren image-detecting device 110. Further, when the calibration fluid CF and the test fluid TF flow through the microfluidic channel AR, a part of the light beam 60 is shielded by the knife-edge 113, and the image-capturing module 114 is able to capture a calibration schlieren image of the calibration fluid CF and a test schlieren image of the test fluid TF flowing through the calibration channel (T-shaped microchannel) and the test channel, respectively.

Moreover, the schlieren image-detecting device 110 further includes a micropositioner 115, which is configured to adjust the cutoff degree of the knife-edge 113 (i.e. the ratio of light beam 60 shielded by the knife-edge 113) by moving the knife-edge 113. For example, in the present embodiment, the micropositioner 115 can move the knife-edge 113 along the direction (y-axis) perpendicular to the transmission path of the light beam 60 and the flowing direction of calibration fluid CF or test fluid TF in the calibration channel or the test channel. In detail, in the present embodiment, the light intensity of a background image acquired by the image-capturing module 114 is mainly controlled by the intensity of the light source 111 and the cutoff degree of the knife-edge 113. When the background image is too bright or too dark, it may change the detectable range of light intensity of the calibration schlieren image and the test schlieren image acquired by the image-capturing module 114, which accordingly influences the sensitivity of the schlieren image-detecting device 110. When the degree of cutoff increases, the sensitivity of the schlieren image-detecting device 110 is increased accordingly, but unwanted diffraction may be produced. Therefore, the cutoff degree of the knife-edge 113 should be adjusted properly by the micropositioner 115, such that the schlieren image-detecting device 110 has proper sensitivity without diffraction.

Moreover, in the present embodiment, the processing unit 130 is electrically connected to the image-capturing module 114 for recording and processing the calibration schlieren image and the test schlieren image. In detail, in the present embodiment, a distance between two positions of the calibration fluid CF respectively corresponding to two neighboring pixels on the calibration schlieren image obtained by the image-capturing module 114 falls within a range from 60 nm to 19.1 μm, and a distance between two positions of the test fluid TF respectively corresponding to two neighboring pixels on the test schlieren image obtained by the image-capturing module 114 falls within a range from 60 nm to 19.1 μm. It should be noticed that the aforementioned ranges of parameters are only used as examples, not to limit the invention.

According to the above descriptions, in the present embodiment, the schlieren image-detecting device 110 can be applied to the microscopic field, which is further described with reference of following FIG. 1C.

Figure 1C:
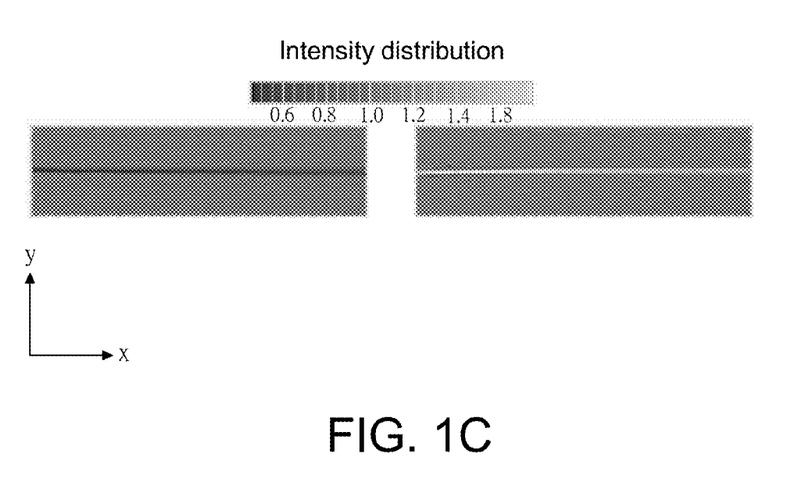
FIG. 1C presents a calibration schlieren image of the embodiment of FIG. 1A.

FIG. 1C illustrates two calibration schlieren images of the embodiment of FIG. 1A. As shown in FIG. 1C, in the present embodiment, a part of the light deflection may dodge the knife-edge 113 or be shielded by the knife-edge 113 to produce the calibration schlieren image with varied light intensities when the calibration fluid CF flows through the space AR. An intensity profile of the calibration schlieren image is, for example, a grayscale distribution. In FIG. 1C, the distribution of the intensity ratio is the ratio between the grayscale readouts of the calibration schlieren image and the grayscale readouts of the background image.

Moreover, the calibration schlieren image shown in FIG. 1C represents multiple pixels and the distance between two neighboring pixels corresponds to a length between 60 nm and 19.1 μm because the pixel pitch of the schlieren image acquired by the image-capturing module 114 is associated to a distance in the calibration fluid CF varying between 60 nm and 19.1 μm. On the other hand, when the fluid analysis system 100 is exploited to analyze the test fluid TF, the distance between two neighboring pixels on the test schlieren image acquired by the image-capturing module 114 also corresponds to a distance in the test fluid TF varying between 60 nm and 19.1 mm. In other words, in the present embodiment, the fluid analysis system 100 has a rather high resolution, which can be applied to the microscopic field.

Figure 2A:
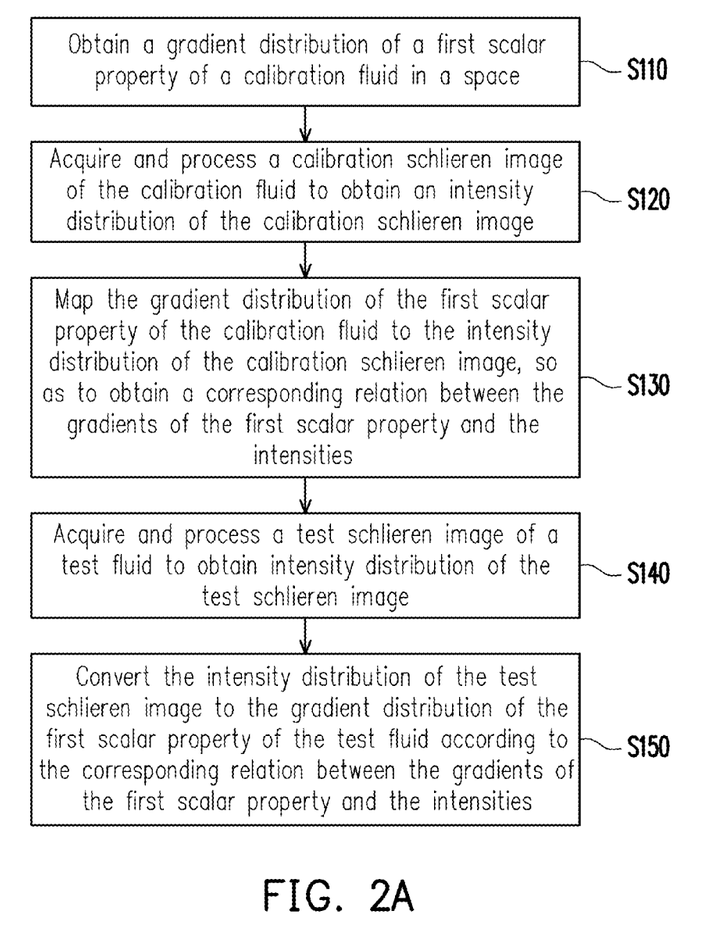
FIG. 2A is a flowchart depicting the fluid analysis method according to an embodiment of the invention.
Figure 2B:
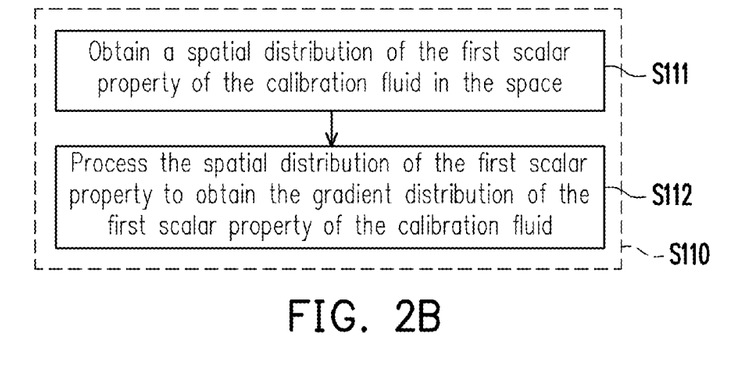
FIG. 2B is a flowchart showing the steps of obtaining a gradient distribution of the first scalar property according to the embodiment of FIG. 2A.

FIG. 2A is a flowchart illustrating a fluid analysis method according to an embodiment of the invention. FIG. 2B is a flowchart depicting steps of obtaining a gradient distribution of the first scalar property according to the embodiment of FIG. 2A. Referring to FIG. 2A and FIG. 2B, in the present embodiment, the fluid analysis method can be, for example, executed by the fluid analysis system 100 of FIG. 1A, though the invention is not limited thereto. Detailed steps of the fluid analysis method of the present embodiment are described below.

First, a gradient distribution of a first scalar property of the calibration fluid CF in the space AR is obtained as shown in step S110. In detail, refractive indices of the calibration fluid CF and the test fluid TF vary linearly with the first scalar property in at least partial interval of the first scalar property. In the present embodiment, the first scalar is concentration, though the invention is not limited thereto. In other embodiments, the first scalar property can also be any other scalar property which varies linearly with the refractive indices of the calibration fluid CF and the test fluid TF in at least partial interval of the first scalar property. For example, if temperature varies linearly with the refractive index of the calibration fluid CF and the test fluid TF in at least partial interval of temperature, the first scalar property of the fluid analysis method of the invention can also be temperature.

Moreover, in the present embodiment, the calibration fluid CF and the test fluid TF are solutions of a single solvent and a single solute, but the invention is not limited thereto. Both the solvents and the solutes of the calibration fluid CF and the test fluid TF are identical. For example, in the present embodiment, the calibration fluid CF and the test fluid TF can be aqueous ethanol solutions with low concentration, and the mass fraction of ethanol in the solution is smaller than 0.25. When the mass fraction of ethanol in the solution is smaller than 0.25, the refractive index of the solution varies linearly with the mass fraction. Hence, the refractive indices of the calibration fluid CF and the test fluid TF vary linearly with the mass fraction in the present embodiment because the corresponding mass fractions fall within this range and the fluid analysis method of the present embodiment is applicable. In detail, the calibration fluid CF consists of a first sub-calibration fluid CF1 and a second sub-calibration fluid CF2 in the present embodiment; the first sub-calibration fluid CF1 and the second sub-calibration fluid CF2 are aqueous ethanol solution with a mass fraction smaller than 0.25 and pure water, respectively. It should be noted that the aforementioned ranges of various parameters are only used as an example, not to limit the invention. For example, the first sub-calibration fluid CF1 and the second sub-calibration fluid CF2 can be aqueous ethanol solutions with different mass fractions in another embodiment. The present fluid analysis method is still applicable to this embodiment as long as the mass fractions of the calibration fluid CF and the test fluid TF are still smaller than 0.25. Moreover, the present fluid analysis method is applicable to other embodiment as long as the refractive indices of the calibration fluid CF and the test fluid TF vary linearly with mass fractions.

Furthermore, the first sub-calibration fluid CF1 and the second sub-calibration fluid CF2 flow into the T-shaped microchannel through entrance EN1 and entrance EN2 respectively, and are mixed in the T-shaped microchannel such that mass fractions of ethanol in solution are different at different positions in the T-shaped microchannel in the present embodiment. The aqueous ethanol solution flows out of the T-shaped microchannel through an exit EX1. Moreover, a non-homogeneous distribution of ethanol is presented in the T-shaped microchannel when the first sub-calibration fluid CF1 and the second sub-calibration fluid CF2 enter through different entrances, creating schlieren patterns on the captured images. For example, a dark strip occurs on the schlieren image similar to that shown in the left part of FIG. 1C when the first sub-calibration fluid CF1 flows in through the upper entrance EN1 and the second sub-calibration fluid CF2 flows in through the lower entrance EN2. In contrast, a bright strip occurs on the schlieren image similar to that shown in the right part of FIG. 1C when the first sub-calibration fluid CF1 flows in through the lower entrance EN2 and the second sub-calibration fluid CF2 flows in through the upper entrance EN1.

In detail, the step S110 in FIG. 2A that obtains the gradient distribution of the first scalar property (i.e. a gradient distribution of concentration) includes sub-steps S111 and S112 in the present embodiment. In the present embodiment, the sub-step S111 and the sub-step S112 can both be executed by the processing unit 130 of the fluid analysis system 100 of FIG. 1A, though the invention is not limited thereto. Referring to FIG. 2B, in the sub-step S111, a spatial distribution of the first scalar property of the calibration fluid CF in the space AR is obtained first. In the present embodiment, 3D computational fluid dynamics (CFD) software can be used to obtain the spatial distribution of the first scalar property of the calibration fluid CF in the space AR as stated in the step S111.

Subsequently, the step S112 is executed, by which the spatial distribution of the first scalar property is processed to obtain the gradient distribution of the first scalar property of the calibration fluid CF. In the present embodiment, the step S112 can be implemented by numerically differentiating the spatial distribution of the first scalar property to obtain the gradient distribution of the first scalar property (i.e. the gradient distribution of concentration) of the calibration fluid CF. In detail, the method of processing the spatial distribution of the first scalar property is, for example, to perform partial differentiation on y, where y is the coordinates perpendicular to the flowing direction as shown in FIG. 1B in the present embodiment.

Subsequently, the step S120 is executed referring to FIG. 2A, by which a calibration schlieren image of the calibration fluid CF is acquired and processed to obtain an intensity distribution of the calibration schlieren image. In the present embodiment, the schlieren image-detecting device 110 of the fluid analysis system 100 of FIG. 1A can be used to acquire the calibration schlieren image of the calibration fluid CF, and the processing unit 130 can be used to process the calibration schlieren image of the calibration fluid CF, so as to obtain the intensity distribution of the calibration schlieren image, though the invention is not limited thereto.

Subsequently, the gradient distribution of the first scalar property of the calibration fluid CF is mapped to the intensity distribution of the calibration schlieren image in step S130, so as to obtain a correlation between the gradients of the first scalar property (i.e. the concentration gradient) and the intensities. In the present embodiment, the step S130 can be executed by the processing unit 130 of the fluid analysis system 100 of FIG. 1A, though the invention is not limited thereto.

Subsequently, a schlieren image of a test fluid is acquired and processed to obtain intensity distribution of the test schlieren image in step S140. In the present embodiment, an execution method of the step S140 is similar to that of the step S120, which is not repeated herein.

Subsequently, the intensity distribution of the test schlieren image is converted to the gradient distribution of the first scalar property of the test fluid TF in step S150 according to the corresponding correlation between the gradients of the first scalar property and the intensities. In the present embodiment, the step S150 can be executed by the processing unit 130 of the fluid analysis system 100 of FIG. 1A, though the invention is not limited thereto. In detail, the geometrical optics theory reveals that the intensities of the calibration schlieren image and the test schlieren image are proportional to gradients of refractive index, so that the intensity distributions of the calibration schlieren image and the test schlieren image also represent the gradient distributions of refractive index. Moreover, the intensity distributions of the calibration schlieren image and the test schlieren image also represent the gradient distribution of the first scalar property because the refractive index varies linearly with the first scalar property in at least a part of the range. Therefore, the related calculation and analysis are performed within the aforementioned at least a part of the range in order to determine the gradient distribution of the first scalar property (i.e. the gradient distribution of concentration) of the test fluid TF from the relation between the gradients of the first scalar property and the intensities obtained by the step S130 and the intensity distribution of the test schlieren image obtained by the step S140.

Figure 3:
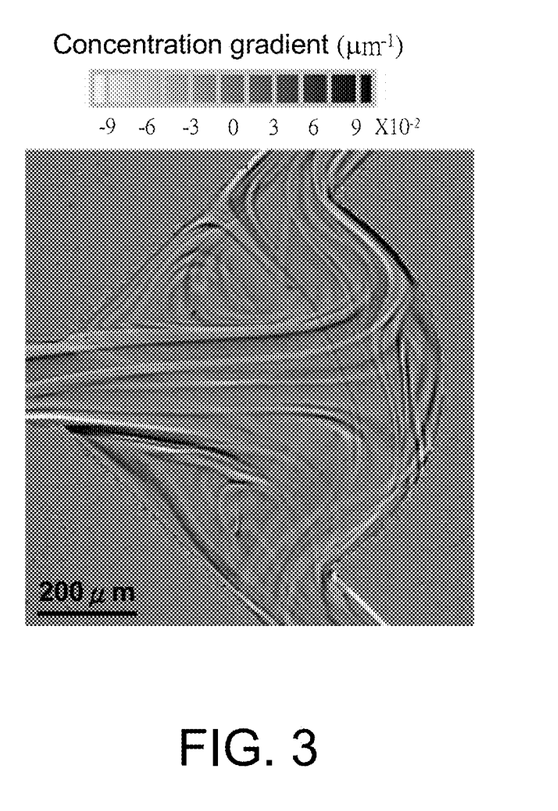
FIG. 3 is a diagram illustrating an implementation of FIG. 2A: a gradient distribution of the first scalar property of a test fluid in a test channel.

FIG. 3 is a diagram illustrating the gradient distribution of the first scalar property of the test fluid as the implementation of FIG. 1A. Referring to FIG. 3, the gradient distribution of the first scalar property of the test fluid TF is determined (as shown in FIG. 3) following the step S150 in the present embodiment, according to the correlation between the gradients of the first scalar property and the intensities obtained through the step S130. The unit of the gradient distribution of the first scalar property (i.e. the gradient distribution of concentration) is the inverse of micrometer ($\mu m^{-1}$). Moreover, distribution of the first scalar property (i.e. concentration) of the test fluid TF in the space AR can be calculated through a numerical integration method with the introduction of a proper boundary condition and calibration curve.

From the corresponding relation between the gradients of the first scalar property and the intensities, the fluid analysis system 100 and the fluid analysis method of the present embodiment are able to deliver the gradient distribution of the first scalar property of the fluid and the 3D flow characteristics presented in more complex flow field. Moreover, the fluid analysis system 100 and the fluid analysis method of the present embodiment is able to reveal details of the microscopic flow field that cannot be obtained through other measurement methods. In general, the fluid analysis system 100 and the fluid analysis method of the present embodiment can be applied to quantitative analysis of the fluid property, so as to provide a non-invasive full-field measurement method for a microscopic mass or heat transfer process.

Figure 4A:
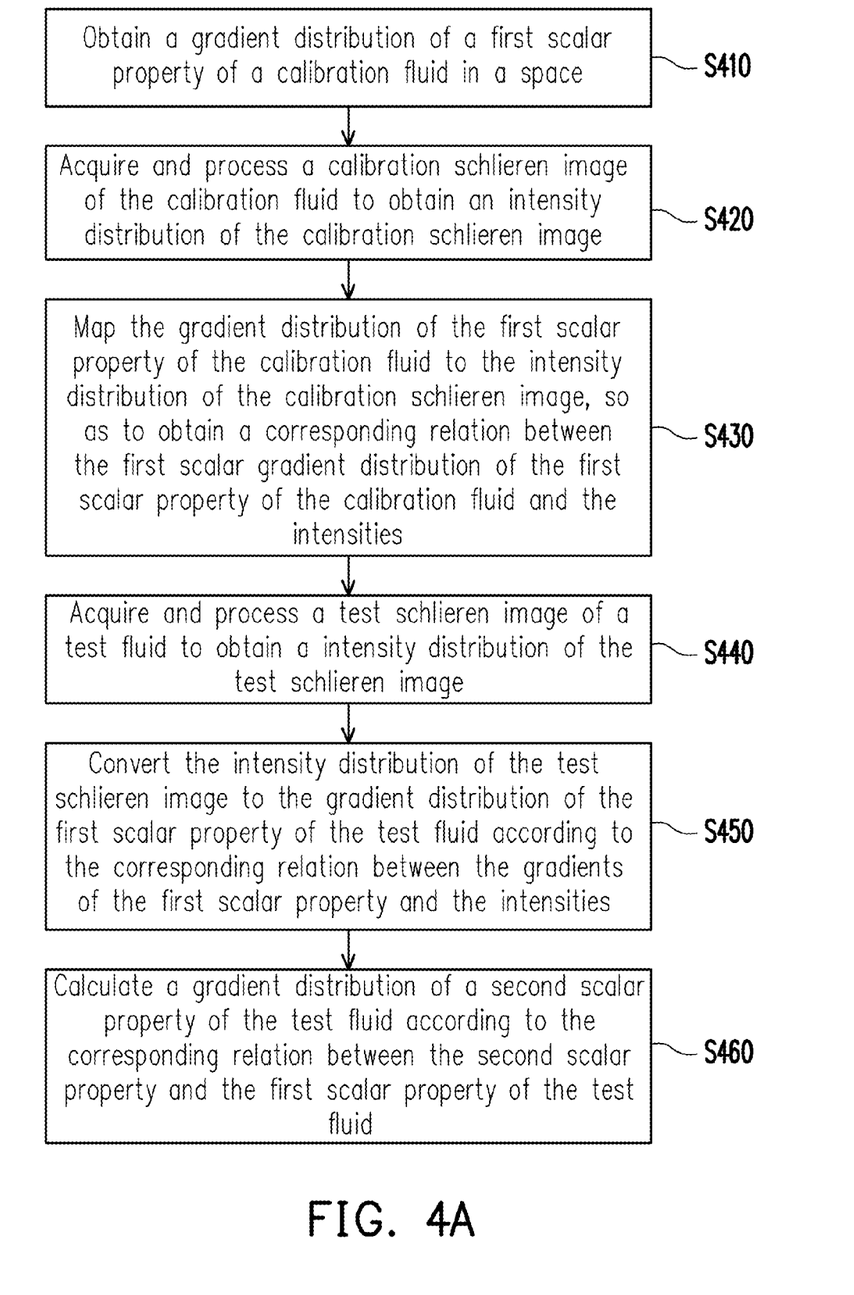
FIG. 4A is a flowchart depicting a fluid analysis method according to another embodiment of the invention.

FIG. 4A is a flowchart depicting a fluid analysis method according to another embodiment of the invention. Referring to FIG. 4A, the fluid analysis method of the present embodiment is similar to the fluid analysis method of the embodiment of FIG. 2A, and differences there between are described below with reference of FIG. 4B.

Figure 4B:
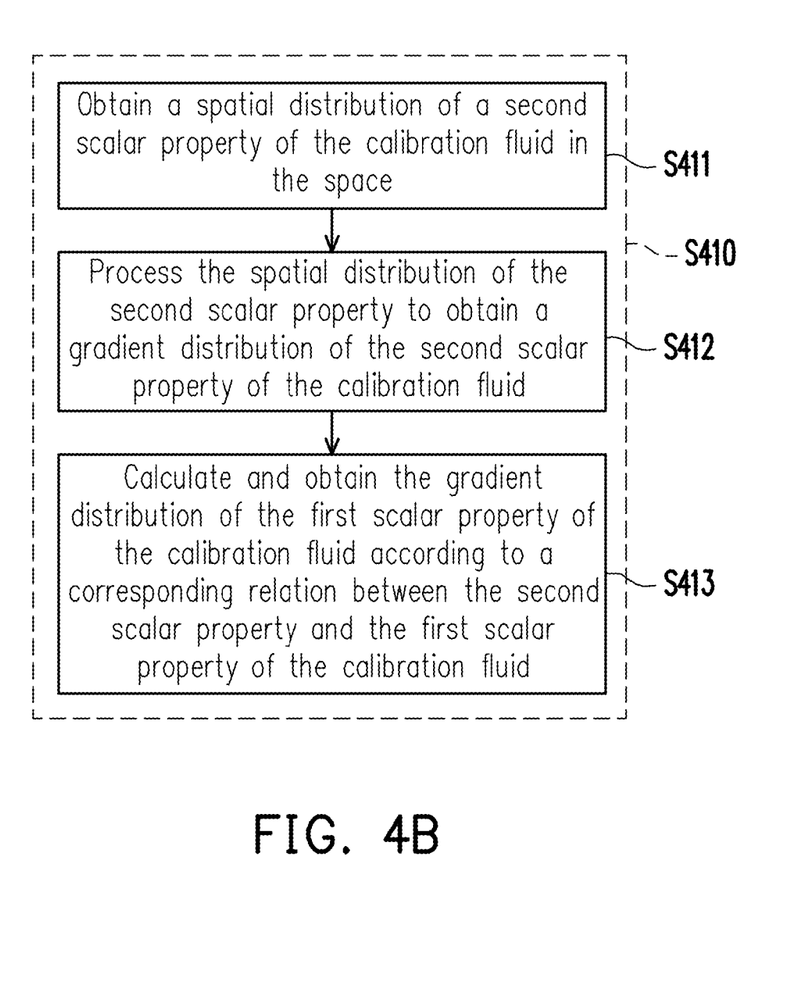
FIG. 4B is a flowchart showing the steps of obtaining a gradient distribution of the first scalar property according to the embodiment of FIG. 4A.

FIG. 4B is a flowchart depicting steps of obtaining the gradient distribution of the first scalar property according to the embodiment of FIG. 4A. In the present embodiment, the first scalar property of the calibration fluid CF and the test fluid TF may not vary linearly with the second property. Herein, the first scalar property is refractive index and the second scalar property is concentration, though the invention is not limited thereto. Moreover, compositions of the calibration fluid CF and the test fluid TF can be identical or different. For example, the calibration fluid CF can be aqueous ethanol solution, and the test fluid TF can be aqueous isopropanol solution, aqueous 2-butanol solution, aqueous 1-butanol solution, aqueous ethylene glycol solution, aqueous acetic acid solution or aqueous butyric acid solution, etc., but the invention is not limited thereto. One can select suitable calibration fluid CF and the test fluid TF according to the practical needs.

Furthermore, the step of obtaining the gradient distribution of the first scalar property (i.e. the gradient distribution of refractive index) of the calibration fluid CF (i.e. the step S410 of FIG. 4A) includes sub-steps S411, S412 and S413 in the present embodiment. Referring to FIG. 4B, first, a spatial distribution of the second scalar property of the calibration fluid CF in the space AR is obtained in the step S411. Subsequently, the spatial distribution of the second scalar property is processed to obtain the gradient distribution of the second scalar property of the calibration fluid CF in the step S412. In other embodiments, the second scalar property can be other scalar properties of the calibration fluid CF and the test fluid TF that can be associated to the corresponding refractive index through a designate relation. Namely, if the corresponding relation between temperature and refractive index of the calibration fluid CF and the test fluid TF is known (for example, by consulting a lookup table, experimental data, model or relation from previous literatures), the second scalar property of the fluid analysis method can also be temperature in the present embodiment. Moreover, the execution of the steps S411 and S412 in the present embodiment are similar to the execution of the steps S111 and S112 in the embodiment of FIG. 2A, and details thereof are not repeated.

Subsequently, in step S413, the gradient distribution of the first scalar property (i.e. the gradient distribution of refractive index) of the calibration fluid CF is calculated according to a corresponding relation between the second scalar property and the first scalar property of the calibration fluid CF. In the present embodiment, the corresponding relation between the second scalar property and the first scalar property of the calibration fluid CF in the step S413 can be obtained by consulting a lookup table, experimental data, model or relation from previous literatures. Moreover, in the present embodiment, the step S413 can be executed by the processing unit 130 of the fluid analysis system 100 of FIG. 1A, though the invention is not limited thereto.

Subsequently, the steps S420, S430 and S440 are executed. The execution of the steps S420, S430 and S440 in the present embodiment are identical to the execution of the steps S120, S130 and S140 of the embodiment of FIG. 2A, and details thereof are not repeated.

Subsequently, the intensity distribution of the schlieren image is converted to the gradient distribution of the first scalar property of the test fluid TF in step S450 according to the corresponding relation between the gradients of the first scalar property (i.e. the gradients of the refractive index) and the intensities. In the present embodiment, the step S450 can be executed by the processing unit 130 of the fluid analysis system 100 of FIG. 1A, though the invention is not limited thereto. In detail, since the intensity distributions of the calibration schlieren image and the test schlieren image are influenced by the variations of refractive index in the space AR, the intensity distributions of the calibration schlieren image and the test schlieren image directly reflects the gradient distribution of the first scalar property (i.e. the gradient distribution of the refractive index) according to the optical principle. Therefore, the gradient distribution of the first scalar property (i.e. the gradient distribution of refractive index) of the test fluid TF can be further obtained according to the corresponding relation of the gradients of the first scalar property (i.e. the gradients of refractive index) and the intensities obtained in the step S430 and the intensity distribution of the test schlieren image obtained in the step S440 in the present embodiment.

Subsequently, a step S460 is executed, by which a gradient distribution of the second scalar property of the test fluid TF is calculated according to the corresponding relation of the second scalar property and the first scalar property of the test fluid TF. In the present embodiment, the corresponding relation of the second scalar property and the first scalar property of the test fluid TF can be obtained by consulting a lookup table, experimental data, model or relation from previous literatures. Moreover, the step S450 can be executed by the processing unit 130 of the fluid analysis system 100 of FIG. 1A in the present embodiment, though the invention is not limited thereto. Furthermore, the gradient distribution of the second scalar property (i.e. the gradient distribution of the concentration) of the test fluid TF is calculated from the gradient distribution of the first scalar property (i.e. the gradient distribution of the refractive index) of the test fluid TF obtained in the step S450 and the corresponding relation of the second scalar property and the first scalar property of the test fluid TF.

Therefore, the fluid analysis method of the embodiment of FIG. 4A may achieve the same effect as that of the fluid analysis method of the embodiment of FIG. 2A, and have the same advantages described in the fluid analysis method of the aforementioned embodiment, which are not repeated herein.

In summary, the fluid analysis system and the fluid analysis method in the embodiments of the invention is able to deliver the gradient distribution of a scalar property of a fluid from the intensity distribution of the schlieren image with the corresponding relation between the gradients of the scalar property and the intensities. In other words, the fluid analysis system and the fluid analysis method in the embodiments of the invention is able to reveal 3D flow structures in the fluid medium based on variations of the refractive index. Moreover, the fluid analysis system and the fluid analysis method of the invention is able to depict details of the microscopic flow field that cannot be obtained through other measurement methods. In general, the fluid analysis system and the fluid analysis method of the invention can be applied to quantitative analysis of fluid property, so as to provide a transient, non-invasive full-field measurement method for microscopic mass or heat transfer process.

It will be apparent to those skill in the art that different modifications and variations can be made in adapting the invention to different embodiments without departing from the broader inventive concepts disclosed herein and comprehended by the claims that follow and their equivalents.

What is claimed is:

1. A fluid analysis method, comprising:
    obtaining a gradient distribution of a first scalar property of a calibration fluid in a space;
    acquiring and processing a calibration schlieren image of the calibration fluid to obtain a light intensity distribution of the calibration schlieren image;
    mapping the gradient distribution of the first scalar property of the calibration fluid to the light intensity distribution of the calibration schlieren image, so as to obtain a relation between gradients of the first scalar property and intensities;
    acquiring and processing a test schlieren image of a test fluid in order to obtain the corresponding light intensity distribution of the test schlieren image, wherein the light intensity distribution of the test schlieren image is converted to the gradient distribution of the first scalar property of the test fluid based on the relation between the gradients of the first scalar property and the intensities.

2. The fluid analysis method as claimed in claim 1, wherein the calibration fluid and the test fluid are solutions, and the first scalar property is concentration.

3. The fluid analysis method as claimed in claim 2, wherein procedures of obtaining the gradient distribution of the first scalar property of the calibration fluid in the space comprise:
    obtaining a spatial distribution of the first scalar property of the calibration fluid in the space; and
    processing the spatial distribution to obtain the gradient distribution of the first scalar property of the calibration fluid.

4. The fluid analysis method as claimed in claim 2, wherein refractive indices of the test fluid vary linearly with the first scalar property of the test fluid in at least part of an interval of the refraction indices.

5. The fluid analysis method as claimed in claim 2, wherein solvents of the calibration fluid and the test fluid are identical, and solutes of the calibration fluid and the test fluid are also identical.

6. The fluid analysis method as claimed in claim 1, wherein procedures of obtaining the gradient distribution of the first scalar property of the calibration fluid comprise:
    obtaining a spatial distribution of a second scalar property of the calibration fluid in the space;
    processing the spatial distribution to obtain the gradient distribution of the second scalar property of the calibration fluid; and
    obtaining a gradient distribution of a first scalar property of the calibration fluid in the space from the gradient distribution of the second scalar property of the calibration fluid in the space with a relation between the first and second scalar properties of the calibration fluid.

7. The fluid analysis method as claimed in claim 6, wherein the gradient distribution of the second scalar property of the test fluid is obtained from the gradient distribution of the first scalar property of the test fluid with the relation between the first and second scalar properties of the test fluid.

8. The fluid analysis method as claimed in claim 6, wherein compositions of the calibration fluid and the test fluid are different; wherein the first scalar property is refractive index, and the second scalar property is concentration or temperature.

9. The fluid analysis method as claimed in claim 1, wherein the first scalar property comprises temperature.

10. The fluid analysis method as claimed in claim 1, wherein the space in which the calibration fluid occupies is a T-shaped microchannel.

11. The fluid analysis method as claimed in claim 1, wherein a method for acquiring the calibration schlieren image or the test schlieren image comprises:
    providing a Hoffman modulation contrast microscope, wherein the Hoffman modulation contrast microscope has a modulator located at a back focal plane of the objective lens of the Hoffman modulation contrast microscope;
    replacing the modulator with a knife-edge to form a schlieren image-detecting device; and
    using the schlieren image-detecting device to acquire the calibration schlieren image or the test schlieren image.

12. The fluid analysis method as claimed in claim 1, wherein the pitch of two adjacent pixels on the calibration schlieren image corresponds to a distance in the calibration fluid ranging from 60 nm to 19.1 µm; wherein the pitch of two adjacent pixels on the test schlieren image corresponds to a distance in the test fluid ranging from 60 nm to 19.1 µm.

13. A fluid analysis system, comprising:
    a schlieren image-detecting device, comprising:
        a light source, providing a light beam;
        an objective lens, disposed on a transmission path of the light beam;
        a knife-edge, disposed on the transmission path of the light beam and located at a back focal plane of the objective lens; and
        an image-capturing module, configured to acquire a calibration schlieren image of a calibration fluid and a test schlieren image of a test fluid; and
    a processing unit, electrically connected to the image-capturing module and configured to record and process the calibration schlieren image and the test schlieren image; wherein the processing unit maps a gradient distribution of the first scalar property of the calibration fluid and a light intensity distribution of the calibration schlieren image so as to obtain correlation between gradients of the first scalar property of the calibration fluid and light intensities; and wherein the processing unit processes the test schlieren image of the test fluid to obtain intensity distribution of the test schlieren image and converts the intensity distribution of the test schlieren image to the gradient distribution of the first scalar property of the test fluid according to the corresponding relation between the gradients of the first scalar property and the intensities.

14. The fluid analysis system as claimed in claim 13, wherein the calibration fluid and the test fluid are solutions, and the first scalar property is concentration.

15. The fluid analysis system as claimed in claim 14, wherein the processing unit obtains the spatial distribution of the first scalar property of the calibration fluid in a space and processes the spatial distribution of the first scalar property to obtain the gradient distribution of the first scalar property of the calibration fluid.

16. The fluid analysis system as claimed in claim 14, wherein refractive indices of the test fluid vary linearly with the first scalar property of the test fluid in at least part of an interval of the refraction indices.

17. The fluid analysis system as claimed in claim 14, wherein solvents of the calibration fluid and the test fluid are identical, and solutes of the calibration fluid and the test fluid are also identical.

18. The fluid analysis system as claimed in claim 13, wherein the processing unit obtains a spatial distribution of a second scalar property of the calibration fluid in a space and processes the spatial distribution of the second scalar property to obtain a gradient distribution of the second scalar property of the calibration fluid; wherein the processing unit obtains the gradient distribution of the first scalar property of the calibration fluid in the space from the gradient distribution of the second scalar property of the calibration fluid in the space with a relation between the first and the second scalar properties of the calibration fluid.

19. The fluid analysis system as claimed in claim 18, wherein the processing unit converts the gradient distribution of the first scalar property of the test fluid to the gradient distribution of the second scalar property of the test fluid with the relation between the first and second scalar properties of the test fluid.

20. The fluid analysis system as claimed in claim 18, wherein compositions of the calibration fluid and the test fluid are different; wherein the first scalar property is refractive index, and the second scalar property is concentration or temperature.

21. The fluid analysis system as claimed in claim 13, wherein the first scalar property comprises temperature.

22. The fluid analysis system as claimed in claim 13, wherein the space in which the calibration fluid occupies is a T-shaped microchannel, and the fluid analysis system also comprises at least one syringe pump in order to drive the calibration fluid into the T-shaped microchannel.

23. The fluid analysis system as claimed in claim 13, wherein a pitch of two adjacent pixels on the calibration schlieren image acquired by the image capture unit corresponds to a distance in the calibration fluid ranging from 60 nm to 19.1 μm; wherein a pitch of two adjacent pixels on the test schlieren image acquired by the image capture unit corresponds to a distance in the test fluid ranging from 60 nm to 19.1 μm.

24. The fluid analysis system as claimed in claim 13, wherein the schlieren image-detecting device also comprises a micropositioner, which is configured to adjust a degree of cutoff for the knife-edge.

* * * * *